United States Patent [19]

Gutek et al.

[11] Patent Number: 4,889,942

[45] Date of Patent: Dec. 26, 1989

[54] PROCESS FOR SYNTHESIS OF ACYLAMINO ORGANOSILICON COMPOUNDS

[75] Inventors: Beth I. Gutek, Freeland; Antony P. Wright, Rhodes, both of Mich.

[73] Assignee: Dow Corning Corporation, Midland, Mich.

[21] Appl. No.: 336,938

[22] Filed: Apr. 12, 1989

[51] Int. Cl.$^4$ .............................................. C07F 7/10
[52] U.S. Cl. ........................................................ 556/419
[58] Field of Search ......................................... 556/419

[56] References Cited

U.S. PATENT DOCUMENTS

| | | | |
|---|---|---|---|
| 2,929,829 | 3/1960 | Morehouse | 556/419 |
| 4,507,455 | 3/1985 | Tanguey et al. | 556/419 X |
| 4,608,270 | 8/1986 | Varagrath | 556/419 X |
| 4,788,310 | 11/1988 | Stein et al. | 556/419 |

*Primary Examiner*—Paul F. Shaver
*Attorney, Agent, or Firm*—Killworth, Gottman, Hagan & Schaeff

[57] ABSTRACT

Organosilicon compounds containing at least one acylamino-substituted hydrocarbon radical are prepared by reacting an organosilicon compound containing at least one amino-substituted hydrocarbon radical with an acyl halide in the presence of a large particle size solid base such as a basic ion exchange resin. A solvent is required only when it is necessary to reduce the viscosity of the reactants.

20 Claims, No Drawings

PROCESS FOR SYNTHESIS OF ACYLAMINO ORGANOSILICON COMPOUNDS

BACKGROUND OF THE INVENTION

This invention relates generally to a method for preparing organosilicon compounds that contain silicon-bonded acylamino-substituted hydrocarbon radicals. More specifically the method involves the reaction of an aminoalkylsilane or siloxane with acyl halides in the presence of a large particle size, solid base.

Organosilicon compounds that contain silicon-bonded acylamino-substituted hydrocarbon radicals are well known and have been described in U.S. Pat. No. 4,608,270 to Varaprath, which is herein incorporated by reference.

As mentioned in Varaprath U.S. Pat. Nos. 4,608,270 and as taught in 2,929,829 to Morehouse, Japan 51/108022 to Furuya et al., Japan 56/74113 to Takamizawa, and West German DE 2365272 to Koetzsch et al., acyl-amino-organo-poly siloxanes can be synthesized by reacting aminosiloxanes with the corresponding acid chloride in the presence of a tertiary amine such as triethylamine. However such a synthesis has several disadvantages. First, the removal of the voluminous precipitate of triethylamine hydrochloride by filtration is tedious. Second, a small amount of HCl is liberated even when an excess of amine is used. This HCl is detrimental to the stability of the polymer, especially when the acid chloride has a reactive vinyl functionality such as where the acid chloride is methacrylyl chloride.

An alternative method for the preparation of acyl-amino-organo-poly-siloxanes involves the reaction of aminosiloxanes and silanes with an acid anhydride or ester at elevated temperature. This is taught in U.S. Pat. No. 4,507,455 to Tangney and Ziemelis, assigned to the assignee of the present invention. Unfortunately at the elevated temperatures of the reaction, acrylamide derivatives undergo Michael addition and amidation of the acrylic double bond resulting in unwanted by-products and crosslinkage of the desired product which ultimately causes the polymer to gel.

Finally as taught in the above-mentioned U.S. Pat. No. 4,608,270 to Varaprath, these problems can be overcome by reacting the aminosilanes and siloxanes with acid chlorides in the presence of an aqueous base such as sodium hydroxide. The HCl that is produced on addition of acyl chloride is neutralized by the hydroxide in the aqueous phase. However, several problems arise from the fact that this reaction is carried out in a two-phase aqueous system in which the aminosiloxane is dissolved in an organic solvent that is immiscible with water. First, the presence of water makes it very difficult to prepare compounds with moisture sensitive functionalities such as methoxy. Second, the presence of metal ions from the base can create a contamination problems. Third, the aqueous base can react with the siloxane bonds in an unwanted manner. Finally, because the amide function is generally highly polar and hydrophilic, it has a tendency to absorb moisture. Incorporation of these units into the siloxane backbone increases water miscibility causing the polymers to emulsify easily thus making phase separation difficult.

To some extent, the latter problem can be overcome by using chlorinated solvents such as methylene chloride or chloroform but, unfortunately, such solvents are environmentally undesirable. Moreover, when larger amounts of amide functionality or more resinous structure or both are used, it is almost impossible to prepare such compounds using a two-phase system even when chlorinated solvents are used.

Accordingly, the need remains for an improved and easier method for preparing acylamino organosilicon compounds that avoids phase separation, base metal ion contamination, filtration, unwanted siloxane bond reactivity, and the solvent toxicity problems previously encountered. The need also remains for an expanded method that permits use of aminosilicon starting materials having hydrolytically unstable groups such as Si-OCH$_3$.

BRIEF SUMMARY OF THE INVENTION

These needs are met by the present invention which is directed to a method for preparing organosilicon compounds that contain at least one silicon-bonded acylamino-substituted hydrocarbon radical by reacting an aminoalkylsilane or siloxane, preferably a primary or secondary aminosiloxane compound with an acyl halide in the presence of a large size, large surface area solid base such as a basic ion exchange resin or granular polyvinyl pyridine.

Preferably the aminosilicon compound is an aminoalkylsilane or siloxane having at least one silicon-bonded amino-substituted hydrocarbon radical containing at least one nitrogen-bonded hydrogen. The silicon-bonded amino-substituted hydrocarbon radical preferably has the formula $-Q(NHQ')_a NZH$ wherein Q and Q' are divalent hydrocarbon radicals. Z is H or a monovalent hydrocarbon radical, and "a" is 0 or 1.

The acyl halide preferably has the formula R"COX where R" is a substituted or unsubstituted monovalent hydrocarbon radical and X is a halogen atom.

The base is a solid, particulate amine, but not a primary or secondary amine. Rather the preferred base is a tertiary aliphatic or aromatic amine or an inorganic supported base. Preferably the particle size must be large enough so that only coarse filtrations are necessary for separation purposes, i.e., a particle size greater than about 10 microns.

The reaction may be carried out at room temperature except where the acyl halide is an acrylyl halide in which case the temperature of the reaction mixture should be lowered to preferably about 0° to 10° C. No solvent is needed if the viscosity of the reactants is sufficiently low. If a solvent is needed to reduce the viscosity of the reactants, an aliphatic, aromatic, or a non-active hydrogen polar solvent is preferably used.

Because a separate aqueous phase is not used. there are no phase separation problems. In addition, the absence of water permits the use of moisture sensitive functionalities such as methoxy. The reaction can be carried out in batch or semi-continuous fashion. Finally because chlorinated solvents are not needed for phase separation purposes, no toxicity problems are encountered.

Additional advantages over prior art systems which utilize strong bases such as alkali metal hydroxides are that the solid basis used in the present invention are easily prepared and are less reactive toward siloxane bonds. Also because an alkali metal hydroxide is not used, there is lower alkali metal contamination potential.

Thus an improved process without many of the drawbacks of the prior art is provided for producing acylamino organosilicon compounds. As described in the Varaprath U.S. Pat. No. 4,608,270, the acylamino organosilicon products are useful for paper release coatings and coupling agents. They are also useful as conformal coatings, for example, as moisture and radiation dual cure coatings of the type disclosed in copending application Ser. Nos. 118,086, filed Nov. 1987 and 200,872, filed June 1, 1988.

Accordingly, it is an object of the present invention to provide an improved method for preparing organosilicon compounds that contain silicon-bonded acylamino-substituted hydrocarbon radicals of the type described in the Varaprath U.S. Pat. No. 4,608,270. These and other objects of and advantages of the invention will become apparent from the following description and the appended claims.

DETAILED DESCRIPTION OF THE PREFERRED EMBODIMENTS

The preferred method consists of reacting an acyl halide with an aminosilicon compound having at least one silicon-bonded amino-substituted hydrocarbon radical containing at least one nitrogen-bonded hydrogen. The remaining silicon bonds are satisfied with organic radicals or divalent, silicon-linking, oxygen atoms, or both. The improved reaction of the present invention is carried out in the presence of a large particle size, solid base. A solvent can be used to reduce the viscosity of the starting material but no solvent is need if the viscosity of the reactants is sufficiently low. The reaction can be carried out at room temperature unless an acrylyl halide is used in which case the reaction is carried out preferably at about 0° to 10° C. The method can be carried out in batch or semi-continuous fashion.

The aminosilicon compound that is to be acylated can have any structure as long as it contains at least one silicon atom bonded to an amino-substituted hydrocarbon radical that bears one or more amino radicals at least one of which has a nitrogen-bonded hydrogen atom. That is, the amino radical must be either a primary or secondary amine. The other silicon bonds are satisfied by organic radicals other than amino-substituted hydrocarbon radicals noted above or by divalent, silicon-linking oxygen atoms. Thus the aminosilicon compound can be a silane, a siloxane, a silcarbane, or a silcarbanesiloxane, although primary or secondary amniosiloxane compounds are preferred.

The silicon-bonded amino-substituted hydrocarbon radical has the formula $-Q(NHQ')_aNHZ$ where Q and Q' denote divalent hydrocarbon radicals, Z denotes a hydrogen atom or a monovalent hydrocarbon radical (R radical) and "a" has a value of 0 or 1.

Examples of Q radicals and Q' radicals include, but are not limited to, alkylene radicals such as ethylene, propylene, isopropylene, butylene, isobutylene, hexylene and octylene and arylene radicals such as phenylene, xylylene, etc. Q is preferably ethylene and Q' is preferably propylene or isobutylene.

Examples of monovalent hydrocarbon radicals (R radicals) include, but are not limited to alkyl radicals such as methyl, ethyl, propyl, butyl, hexyl, and octyl; cycloaliphatic radicals such as cyclohexyl: aryl radicals such as phenyl, benzyl, styryl, tolyl, and xenyl; and alkenyl radicals such as vinyl and allyl.

Thus, examples of amino-substituted hydrocarbon radicals include, but are not limited to, $NH_2CH_2CH_2CH_2-$, $CH_3NHCH_2CH_2CH_2-$, $NH_2CH_2CH(CH_3)CH_2-$, $NH_2CH_2CH_2NHCH_2CH_2CH_2-$, $NH_2CH_2CH_2NHCH_2CH(CH_3)CH_2-$, $NH_2(CH_2)_6NH(CH_2)_3-$, and $NH_2(CH_2)_6NHCH_2CH(CH_3)CH_2-$.

Silicon-bonded radicals, other than the above-noted amino-substituted hydrocarbon radicals, include organic radicals and divalent, silicon-linking, oxygen atoms. Examples of said organic radicals include, but are not limited to, divalent, silicon-linking hydrocarbon radicals such as the Q and Q' radicals noted above, and halogenated derivatives thereof, monovalent hydrocarbon radicals, such as those noted above, and halogenated derivatives thereof, alkoxy radicals such as methoxy radicals, hydroxy radicals, aryloxy radicals and hydrogen atoms. Preferably said organic radicals contain no more than 6 carbon atoms, such as methyl, 3,3,3-trifluoropropyl. phenyl, methoxy and vinyl radicals, and most preferably are methyl radicals.

The aminosilicon compounds to be acylated by the process of this invention are preferably silanes or siloxanes having the average formula $R'_c(NH_2(Q'NH)_aQ)_dSiO_{(4-c-d)/2}$ where R' denotes a monovalent hydrocarbon radical or an alkoxy radical as defined above, "c" denotes a number having a value of from 0 to 3, such as 0, 0.5, 1.01, 2, 2.1, and 3, "d" denotes a number having a value of from >0 to 4, such as 0.01, 0.5, 1, 2, and 3, and "c"+"d" has a value of from 1 to 4 such as 1.5, 1.99, 2.01, 3 and 4. Of course, the aminosilane or siloxane must contain an average of at least one silicon-bonded, amine-substituted hydrocarbon radical per molecule, Q and Q' are as defined above. The siloxanes can contain siloxane units that are free of amino-substituted hydrocarbon radicals such as $R'_cSiO_{(4-c)/2}$ such as $MeSiO_{3/2}$, $PhSiO_{3/2}$, $PhMeSiO_{2/2}$, $Me_2SiO_{2/2}$, $Me_3SiO_{1/2}$, $MeViSiO_{2/2}$, $Me_2(OMe)SiO_{1/2}$, $Ph_2SiO_{2/2}$, $(MeO)_3SiO_{1/2}$, $ViMe_2SiO_{1/2}$, and $SiO_{4/2}$ units, in addition to siloxane units that contain the required amino-substituted hydrocarbon radicals. Herein the symbols Me, Ph and Vi denote methyl, Phenyl and vinyl, respectively.

Preferred aminosilanes to be acylated have the formula $R'_eSi(QNHCH_2CH_2HN_2)_{4-e}$ where "e" denotes a number having a value of 0, 1, 2, or 3, e.g., an aminosilane such as $Me_3SiCH_2CH(CH_3)CH_2NHCH_2CH_2NH_2$.

Preferred aminosiloxanes to be acylated have the formula $YR'_2SiO(R_2SiO)_x(YR'SiO)_ySiR'_2Y$ where each Y denotes, independently, an R' radical or a $-QNHCH_2CH_2NH_2$ radical and x and y denote numbers having average values of from 0 to 5000 and 0 to 500, respectively. Examples of preferred aminosiloxanes to be acylated include, but are not limited to, $Me_3SiO(Me_2SiO)_{500}(MeYSiO)_2SiMe_3$, $YMe_2SiO(Me_2SiO)_{2000}SiMe_2Y$, $YMe_2SiO(Me_2SiO)_{100}(MeYSiO)_3SiMe_2Y$, $Me_3SiO(MeYSiO)_1SiMe_3$, $YMe_2SiO(MeYSiO)_1SiMe_2Y$, $Y(MeO)_2SiO(Me_2SiO)_x(PhMeSiO)_ySi(OMe)_2Y$, and $Y(MeO)_2SiO(Me_2SiO)_x(Ph_2SiO)_ySi(OMe)_2Y$.

For conformal coatings, the preferred structure is $Y'(OMe)_2SiO(Y'MeSiO)_xSi(OMe)_2Y'$ where "x" is 0 to 500 and Y' is a Me or MeO radical or a $-Q(Q'NH)_aNHMe$ radical where Q is preferably a divalent propylene or butylene radical Q' is a divalent ethylene radical, and "a" is 0 or 1.

Aminosiloxanes can also have a cyclic or branched structure such as $(YMe_2SiO)_4Si$ and $(YMeSiO)_4$, in addition to the linear structures noted above.

Aminosilicon compounds and their preparation are well known in the organosilicon art. Some are commercially available. The disclosures of U.S. Pat. Nos. 2,557,803, 2,738,357, 2,754,312, 2,762,823, 2,998,406, 3,045,036, 3,087,909, 3,355,424, 3,560,543, 3,890,269, 4,036,868, 4,152,346, and 4,507,455 are incorporated herein by reference to further teach how to prepare aminosilicon compounds that can be used in the method of this invention.

The acyl halide can have any structure such as a linear, branched, or cyclic structure having aromatic, heterocyclic, olefinic or paraffinic bonding and containing one or more carbon-bonded —COX radicals, where X denotes a halogen atom. Preferably the acyl halide has the structure R″ COX where X denotes a halogen atom. Preferably chlorine, and R″ denotes a substituted or unsubstituted monovalent hydrocarbon radical.

Examples of unsubstituted monovalent hydrocarbon radicals include, but are not limited to, those delineated above for monovalent hydrocarbon radicals. Examples of corresponding acyl halides include acetyl chloride, benzoyl chloride and, most preferably, acrylyl chloride. methacrylyl chloride, and cinnamoyl chloride, Examples of substituted monovalent hydrocarbon radicals include, but ar not limited to, halogenated radicals such as —CF$_3$ and —C$_6$H$_4$Cl, and other substituted radicals which are stable under the reaction conditions employed in the method of this invention such as —CH$_2$CH$_2$CN, —C$_6$H$_4$NO$_2$ and —C(CN)=CH$_2$.

The acyl halide is added to a mixture of the aminosilicon compound, a nonaqueous solvent, and a stoichiometric excess amount of solid base. Preferably the solid base has a large particle size and a large surface area. Preferably the base can be any basic amine that is not a primary or secondary amine, preferably tertiary aliphatic and aromatic amines and inorganic supported bases such as Amberlyst-21 (a polystyrene ion exchange resin bearing dimethylamino groups; Rohm & Haas, Philadelphia, PA). basic Amberlyst-27 (a polystrene ion exchange resin bearing trimethylammonium hydroxide groups), and Reilex 425 (Polyvinyl Pyridene).

A nonaqueous solvent can be used to dissolve the aminosilicon compound and the acyl halide to be added to it. The solvent is used to reduce viscosity and to improve mixing. The solvent can be any suitable nonaqueous liquid that will not react with the components of the reaction, The solvent can be an aliphatic, aromatic, or a non-active hydrogen polar solvent. Preferably the solvent is also a solvent for the organoslicon product of the reaction, Examples of suitable solvents include, but are not limited to, hydrocarbons such as toluene, xylene, hexane, cyclohexane and heptane: halogenated hydrocarbons such as methylene chloride, chloroform, trichloroethylene and trichloroethane; and oxygenated compounds such as ethyl ether and ethyl acetate. Mixtures of two or more solvents can also be used, it only being required that the mixture, and not necessarily all of the components in the mixture, be a solvent for the aminosilicon compound, preferably non-regulated solvents such as toluene or hexane are used, The amount of solvent that is used should be sufficient to dissolve the aminosilicon compound and, preferably, the organosilicon product as well. If the reactants are of sufficiently low viscosity no solvent at all may be needed, The necessary components of the reaction mixture, i.e., the acyl halide, the aminosilicon compound and the solid base can be mixed in any manner as long as the acyl halide is added to the aminosilicon compound in the presence of the solid base. In a preferred embodiment, the acyl halide or a solution thereof is added to a well agitated mixture of the aminosilicon material or a solution thereof and the solid base, preferably the aminosilcon compound, the solid base, and the acyl halide are used in about stoichiometric amounts.

A deficiency of acyl halide relative to the total number of acylatable amino groups, although merely leading to the preparation of incompletely acylated product when the acyl halide is free of aliphatic unsaturation, leads to products which can undergo a Michael-Addition type reaction when the acyl halide contains aliphatic unsaturation. For this reason, it is preferred, although not required, to fully acrylate the aminosilicon compound when an acrylyl halide is used. A deficiency of the solid base relative to the amount of hydrogen halide produced is to be avoided, preferably spent base is exchanged for fresh base to avoid the presence of HCl since HCl is detrimental to the stability of acylaminopolysiloxanes, especially when the acid chloride has a reactive vinyl functionality such as where the acid chloride is methacrylyl chloride, Except when the acyl halide is an acrylyl halide, the method of this invention can be practiced at any reasonable temperature. Advantageously, this method proceeds readily at room temperature, When an acrylyl halide is used, this method should be practiced at as low a temperature as possible to minimize the formation of byproducts. Accordingly, when using the method of this invention to prepare acrylyl-substituted aminosilicon compounds, the reaction should be conducted at a temperature of from 0° to 10° C. Lower reaction temperatures are suitable but higher reaction temperatures will substantially reduce the yield of desired product.

During and after the addition of the acyl halide component to the aminosilicon component, the reaction mixture should be thoroughly agitated to maintain intimate contact between the alkaline material and the hydrogen chloride reaction product. The usual low shear means such as stirrers, paddles, and impellers are sufficient to maintain sufficient agitation. Agitation is maintained until the acylation reaction is finished, typically within an hour.

When a solvent is used, the product of the reaction can be separated after the reaction is finished by stripping off the solvent, When acrylyl-substituted products are to be separated from the solvent, it is desirable to add a polymerization inhibitor such as sodium nitrite or phenothiazine to the solution prior to any separating action such as distilling or fractionation.

The reaction can be carried out in either a batch or semi-continuous fashion. In a batch reaction, the aminosilicon compound, a nonaqueous solvent, and the solid base are mixed together. The acyl halide is added rapidly to the mixture with stirring and the liquid poured immediately into a clean vessel with fresh solid base, After stirring briefly, the base is separated and the solvent removed.

In a semicontinuous reaction, metered amounts of aminosilicon compound and acyl chloride are added simultaneously with continuous stirring to a vessel containing the solid base. The liquid is then allowed to flow through a column packed with base. On emerging from the column, the product is stripped of solvent.

The products of this method are useful as polar silicon-containing additives for cosmetic compositions, coating compositions, textile treating compositions, and paints. The compositions are useful as comonomers with polymerizable vinyl monomers such as styrene, butadiene, methyl methacrylate, ethyl acrylate, vinyl acetate, vinyl chloride, vinylidene chloride and acrylonitrile. In particular the compounds having acrylylamine-substituted hydrocarbon radicals are useful as a reactive component in free radical curable compositions such as radiation curable compositions used for paper, resin protective, and optical fiber coatings.

The following examples are disclosed to further teach the practice of the invention and are not intended to limit the invention as t is delineated in the claims.

EXAMPLE 1

This example illustrates the preparation of $(MeO)_3SiPrNHCOCH=CH_2$. Amberlyst 21 (133.5 g; 0.642 mole) was washed with 200 ml of methanol twice followed by three washings with 200 ml of methylene chloride. The Amberlyst 21, 100 g (0.559 mole) of $(MeO)_3SiPrNH_2$, and 150 g of methylene chloride were mixed in a 3-necked. round-bottom flask fitted with an addition funnel, $N_2$ inlet, and stirrer. Fifty grams of acrylyl chloride (0.556 mole) was mixed with 50 g of methylene chloride and placed in the addition funnel. The flask was cooled to $-5°$ C. and the acrylyl chloride added dropwise with stirring while maintaining the temperature of the reaction flask between about $-5°$ and $+5°$ C. The reaction was stirred for an additional 15 minutes after which the Amberlyst was strained off and the solvent stripped under vacuum. The product was a light brown liquid with a viscosity of 380 cps.

EXAMPLE 2

This example illustrates the preparation of $CH_2=CHCONMeBuSiMe_2O(Me_2SiO)_{300}SiMe_2BuNMeCOCH=CH_2$. The general procedure of Example 1 was used with 80.0 g (0.007 moles) of $NHMeBuSiMe_2O(Me_2SiO)_{300}SiMe_2BuNHMe$. 87.2 g of dry toluene, and 19.0 g (0.100 moles) of Amberlyst 21. Acrylyl chloride (7.17 g; 0.079 moles) and 8 g of toluene were added from the addition funnel after which the reaction mixture was allowed to warm to room temperature and stirred for 30 min. The solution was then poured through a fresh 19 gram batch of Amberlyst 21 after which the product was stripped of solvent.

EXAMPLE 3

This example illustrates the preparation of an acrylamide siloxane fluid. A silanol-enblocked polydimethylsiloxane (1776 g; 1.6 moles) was dried by heating to 130° C. with rapid stirring and a nitrogen purge. Propylamino trimethoxy silane (360 g). a 2% phenothiazine solution (toluene; 45.9 g) a 10% p-methoxy phenol solution (toluene; 10.8 g) and a 0.1N potassium hydroxide solution (methanol) were mixed with the dried silanol-enblocked polydimethylsiloxane and heated to 130° C. A stoiciometric amount of methanol was collected plus the methanol from the KOH solution. The product solution was cooled to room temperature, neutralized with acetic acid and filtered through a 0.45 micron membrane filter. The aminosiloxane product had an amine neutral equivalent of 1,057 and a viscosity of 26 cs.

One hundred grams of toluene. 65 g Rilex 425 (polyvinyl pyridene 0.357 moles) and 0.75 sodium nitrite were mixed in a three-necked flask and dried by refluxing using a Dean Stark trap. One hundred grams (0.095 moles) of the aminosiloxane fluid was added to the mixture and cooled to about 0° to $-5°$ C. with an isopropanol-dry ice bath. Equal amounts (12.85 g) of toluene and acrylyl chloride were mixed. Placed in a dropping funnel, and added dropwise over a period of about 30 minutes with rapid stirring. Stirring was continued while the mixture was allowed to warm to room temperature. Stirring was discontinued and the mixture allowed to sit over night. The mixture was then filtered through #1 grade Whatman filter paper to remove the Rilex 402 which was then rinsed with toluene to remove any remaining product. The toluene solution of the product was filtered through a 0.22 μm membrane filter equipped with a prefilter. Phenothiazine (0.5 g) was added to the filtered solution and the solvent was stripped at 65° C. using a rotovac. The resulting acrylamide fluid had a viscosity of 1500 cps.

That which is claimed is:

1. A method for preparing an organosilicon compound containing at least one silicon-bonded acylamino-substituted hydrocarbon radical comprising: reacting an acyl halide with an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent, silicon-linking, oxygen atoms, in the presence of a solid base selected from group consisting of a tertiary aliphatic amine resin, a tertiary aromatic amine resin, an inorganic supported base, a polystyrene ion exchange resin bearing dimethylamino groups, a polystyrene ion exchange resin bearing trimethylammonium hydroxide groups and a polyvinyl pyridine.

2. The method according to claim 1 wherein said silicon-bonded amino-substituted hydrocarbon radical has the formula $-Q(NHQ')_aNZH$ and the acyl halide has the formula $R''COX$, wherein Q and Q' denote divalent hydrocarbon radicals, R" denotes a substituted or unsubstituted monovalent hydrocarbon radical, X denotes a halogen atom, Z denotes a hydrogen or a monovalent hydrocarbon radical, and "a" has a value of 0 or 1.

3. The method according to claim 2 wherein said acyl halide is a compound selected from the group consisting of $CH_2=CHCOCl$, $CH_2=C(CH_3)COCl$, and $C_6H_5CH=CHCOCl$.

4. The method according to claim 3 wherein said aminosilicon compound has the average unit formula $R'_c(NH_2(Q'NH)_dQ)_dSiO_{(4-c-d)/2}$ wherein R' denotes a monovalent hydrocarbon radical or an alkoxy radical.

"c" has a value of from 0 to 3,

"d" has a value of $>0$ to 4, and

"c"+"d" has a value of 1 to 4.

5. The method according to claim 4 wherein said aminosilicon compound is a siloxane having the formula $YR'_2SiO(R_2SiO)_x(YR'SiO)_ySiR'_2Y$ wherein Y denotes R' or $-QNHCH_2CH_2NH_2$, x has a value of from 0 to 5000, and y has a value of from 0 to 500.

6. The method according to claim 4 wherein said aminosilicon compound is a silane having the formula $R'_eSi(QNHCH_2CH_2HN_2)_{4-e}$ wherein e has a value of 0, 1, 2, or 3.

7. The method according to claim 4 wherein R' is selected from the group consisting of methyl, phenyl, vinyl, and methoxy.

8. The method according to claim 1 wherein said aminosilicon compound is a siloxane having the formula Y'(OMe)$_2$SiO(Y'MeSiO)$_x$Si(OMe)$_2$Y' wherein
x is 0 to 500 and
Y' is a Me or MeO radical or a —Q(NHQ')$_a$NHMe radical wherein
Q is a propylene or butylene radical,
Q' is an ethylene radical, and
"a" is 0 or 1.

9. The method according to claim 1 wherein said acyl halide is added to a mixture of said aminosilicon compound and solid base.

10. The method according to claim 9 wherein the resulting mixture obtained by adding said acyl halide is agitated until the compound is formed.

11. The method according to claim 1 wherein said reaction is carried out in the presence of a nonaqueous solvent.

12. The method according to claim 11 wherein said solvent is toluene.

13. The method according to claim 11 further comprising isolating the organosilicon compound containing at least one silicon-bonded acylamino-substituted hydrocarbon radical.

14. The method according to claim 1 wherein said reaction is carried out at a temperature of from about −5° to +5° C.

15. The method according to claim 1 wherein the molar amount of said solid base is at least equal to the molar amount of said acyl halide.

16. The method according to claim 1 wherein the molar amount of said acyl halide is in about 5% molar excess over the molar amount of reactive nitrogen-bonded hydrogen atoms of said aminosilicon compound.

17. The method according to claim 1 wherein the reaction is carried out with continuous stirring.

18. The method according to claim 1 wherein spent solid base is removed and replaced with fresh solid base.

19. The method according to claim 1 wherein said acyl halide and said aminosilicon compound are added simultaneously to a nonaqueous solution of said solid base and the resulting solution allowed to pass over a packed column of said solid base.

20. The method according to claim 1 wherein said solid base has a particle size of greater than about 10 microns.

* * * * *